Figure 1:
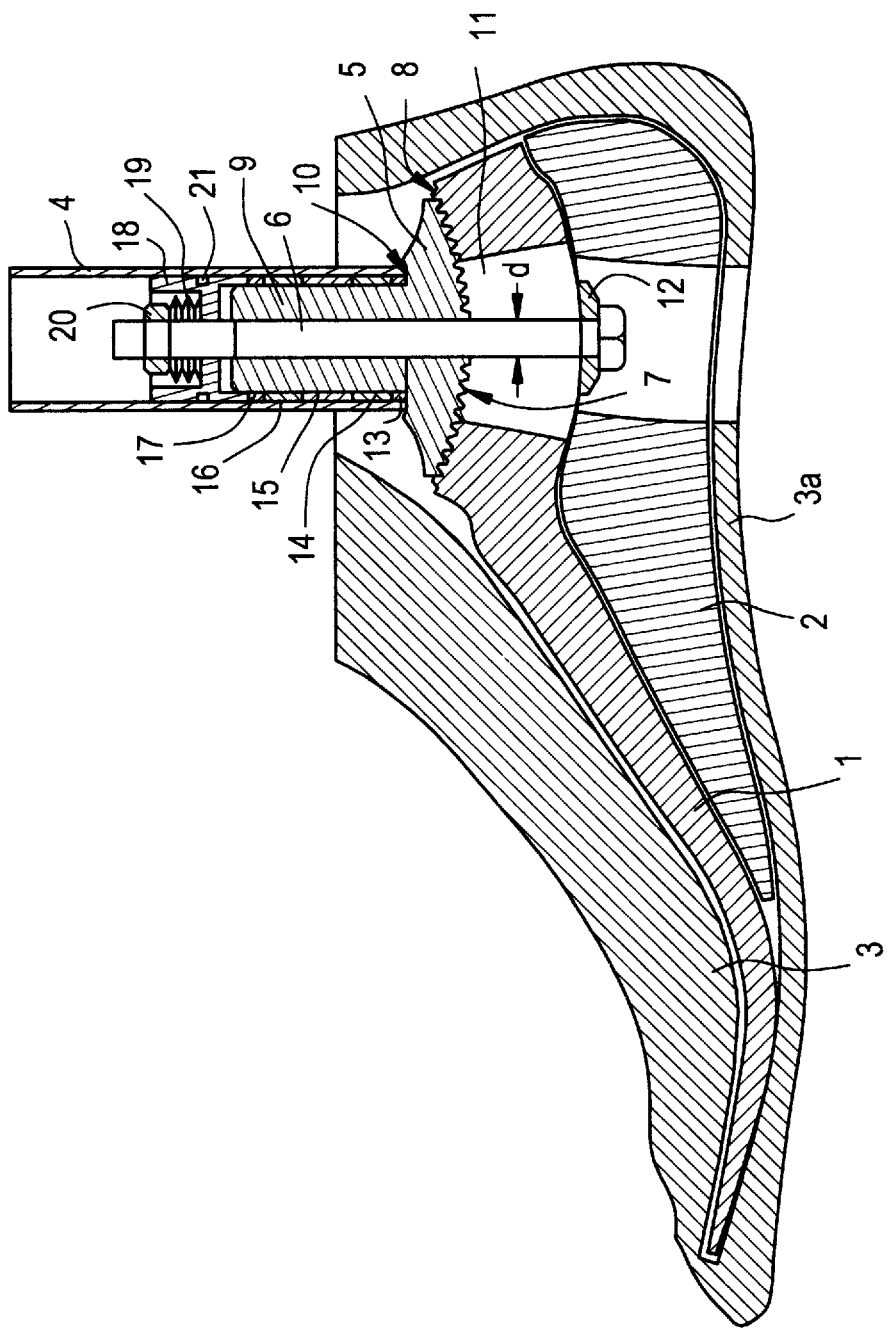

United States Patent [19]
Wellershaus et al.

[11] Patent Number: 5,888,239
[45] Date of Patent: Mar. 30, 1999

[54] JOINTLESS FOOT PROSTHESIS

[75] Inventors: Ulf Wellershaus; Kai Leppack, both of Duderstadt, Germany

[73] Assignee: Otto Bock Orthopaedische Industrie Besitz-Und Verwaltungs-Kommanditge-Sellschaft, Duderstadt, Germany

[21] Appl. No.: 894,693

[22] PCT Filed: Jun. 5, 1996

[86] PCT No.: PCT/DE96/01031

§ 371 Date: Aug. 26, 1997

§ 102(e) Date: Aug. 26, 1997

[87] PCT Pub. No.: WO96/41598

PCT Pub. Date: Dec. 27, 1996

[30] Foreign Application Priority Data

Jun. 9, 1995 [DE] Germany ................. 195 21 147.2

[51] Int. Cl.$^6$ ........................................ A61F 2/66
[52] U.S. Cl. ............................ 623/55; 623/47
[58] Field of Search ................. 623/47–56, 27

[56] References Cited

U.S. PATENT DOCUMENTS 4,463,459  8/1984  Shorter et al. ................. 623/47
5,112,356  5/1992  Harris et al. ................... 623/49

FOREIGN PATENT DOCUMENTS 2148322  7/1971  France ................. 623/47

Primary Examiner—Paul B. Prebilic
Assistant Examiner—Bruce E. Snow
Attorney, Agent, or Firm—Foley & Lardner

[57] ABSTRACT

A foot prosthesis has an inner spring that extends from the heel area to the front area of the foot. The foot spring is enclosed within a cosmetic lining and is joined by a threaded bolt to an adapter with a clamping connection for removably joining the foot prosthesis to a prosthesis tube. The adapter is supported by its lower face, which is designed as a cylinder segment and is provided with serrations, on a joining surface of the inner spring. The joining surface of the inner spring has a shape corresponding to the lower face of the adapter, and has serrations for engaging the adapter's serrations. The upper end of the adapter is designed as a peg which is inserted into the prosthesis tube. The threaded bolt is inserted through a slot that extends in the longitudinal direction of the foot and has a width corresponding to the diameter of the bolt. The lower end of the threaded bolt is supported on the lower side of the inner spring, the lower side being designed as a cylinder segment in the area of the slot. The upper end of the threaded bolt that projects above the adapter peg acts upon the clamping connection such that the spreading element of the clamping connection, which is arranged in a ring-shaped gap between the adapter peg and the prosthesis tube, is actuated when the threaded bolt is tightened.

5 Claims, 2 Drawing Sheets

JOINTLESS FOOT PROSTHESIS

The invention relates to a jointless foot prosthesis with an internal foot spring extending from the heel to the forefoot, which is contained within a cosmetic covering and is connected by a bolt to an adapter which has a clamping means for releasable attachment to a prosthesis tube.

An embodiment of this kind can be found, for example, in U.S. Pat. No. 4,645,509. The adapter in this embodiment is drawn by the bolt tightly against an upper abutment surface of the internal foot spring and is disposed undisplaceably with respect to the latter. The adapter has a clamping sleeve into which the bottom end of the tube of the lower leg prosthesis can be inserted and can be clamped tightly by tightening a separate clamping screw.

U.S. Pat. No. 5,122,356 discloses a foot prosthesis equipped with a ball joint, having an internal foot spring which extends from the heel to the forefoot, is contained within a cosmetic covering, and is connected by a bolt to an adapter which forms the lower part of the ball joint whose upper member is integrated into the bottom end of a slotted clamping sleeve serving for releasable attachment to a prosthesis tube. The adapter rests with its bottom, configured as a cylinder segment and provided with serrations, upon a mating face of the internal foot spring whose serrations mesh with the serrations of the adapter. The bolt is passed through a slot in the internal foot spring which has a width corresponding to the diameter of the bolt and runs lengthwise of the foot, and at its bottom end the bolt thrusts against the bottom of an upper horizontal leg of the internal foot spring through a cylinder segment extending over the width of the slot. The ball joint can be removed from the adapter only by completely unscrewing the bolt.

FR 2.148.322 discloses a jointless foot prosthesis which has no internal foot spring but has a wooden core on which a cylinder segment is fastened by screws; the partially cylindrical wall of the cylinder segment is provided at its open top with serrations on which the bottom of an adapter is supported which is configured as a cylinder segment and provided with serrations, the two serrations being in mesh with one another. The upwardly projecting end of the adapter is provided with a recess into which the bottom end of a prosthesis tube is inserted. To serve as a clamping means, a slotted sleeve is inserted into the bottom end of the prosthesis tube and has an inner wall tapering from top to bottom, and in it there is guided a locking nut whose level is adjustable through a bolt passed from below through the wooden core and the two cylinder segments. When the bolt is tightened the locking nut is drawn downwardly, thereby spreading the split tube, thus forcing the prosthesis tube and the wall of its bottom end against the inner wall of the recess in the adapter.

This clamping attachment has the disadvantage that the clamping requires an expansion of the bottom end of the prosthesis tube, so that only appropriately thin-walled prosthesis tubes, or else only slotted prosthesis tubes, can be used. Mainly, however, the expansion of the tube in this area leads to fatigue fracture during the use of the foot prosthesis. Also, the expansion of the prosthesis tube does not take place uniformly over a sufficiently long section thereof. Since the actual clamping attachment has to take place between the outer wall of the tube and the inner wall of the adapter, although the adapter has to be made very rigid, a load-bearing damping surface can hardly be assured. High damping pressure can result in the cracking of the tube under flexural stress.

The invention is addressed to the problem of improving the function of the foot prosthesis described above.

This problem is solved according to the invention in conjunction with the features listed in the beginning, by the following additional features.

a) The adapter rests with its bottom, configured as a cylinder segment and provided with serrations, on a mating surface of the internal foot spring whose serrations are in mesh with the adapter.

b) The upper end of the adapter is configured as a shank onto which the prosthesis tube is fitted.

c) The bolt is passed through a slot provided in the internal foot spring and having a width corresponding to the bolt diameter, and with its bottom end it thrusts against the bottom of the internal foot spring which is also given the shape of cylinder segment in the slot area.

d) The upper end of the bolt extends above the adapter shank and produces the said attachment, which involves a spreader means disposed in an annular gap between the adapter shank and the prosthesis tube and acted upon by tightening the bolt.

e) The spreader means has at least one elastomer ring (14, 16) whose bottom rests directly or indirectly on an abutment surface (10) of the adapter (5) and is driven at its top by a driver (18) which is guided on the adapter shank (9) and driven by the bolt (6) in the axial direction of the latter.

This foot prosthesis according to the invention makes it possible, by means of the locking adjustment, to set different heel levels. The centering and locking on the prosthesis tube are accomplished by the aforesaid spreader means.

To improve the centering of the prosthesis tube, to protect the elastomer ring, and to provide for equalization of length with respect to the driver, the elastomer ring is disposed between an intermediate ring and an end ring.

To maintain a specific tensile force lengthwise of the bolt it is advantageous if the bolt thrusts against the driver through a spring means.

Additional features of the invention are the subject of the subordinate claims and will be further explained along with additional advantages of the invention with the aid of an embodiment.

Figure 2:
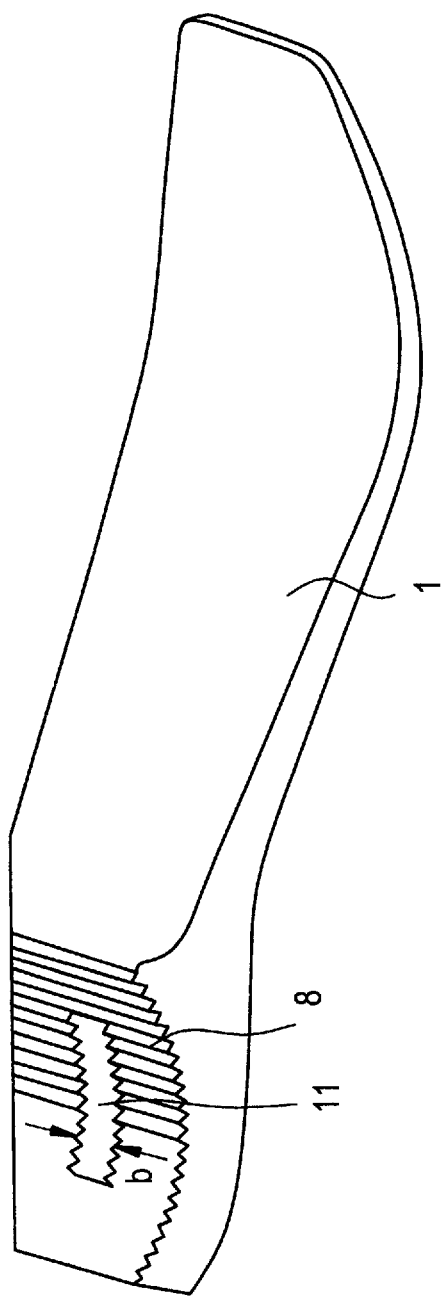

An embodiment of the invention serving as an example is shown in the drawing, wherein:

FIG. 1 is a perpendicular longitudinal section through a foot prosthesis with attached prosthesis tube, and FIG. 2 is a perspective representation of the internal foot spring according to FIG. 1, but in a position rotated 100° in relation to FIG. 1.

The foot prosthesis represented comprises essentially an internal foot spring 1 reaching from the heel into the forefoot and resting on a replaceable insert wedge 2 which is held between the internal foot spring 1 and the bottom 3a of a cosmetic cover 3 surrounding internal foot spring 1 and insert wedge 2. The cover 3 can be in the form of a foam mask, a foam mask with a reinforced sole, or a shoe or sandal.

The foot prosthesis is joined to a prosthesis tube 4 of a lower leg prosthesis by an adapter 5 and a bolt 6 extending through the latter.

The adapter 5 is supported at its bottom, configured as a cylinder segment bearing serrations 7, on a mating surface of the internal foot spring 1 whose serrations 8 mesh with the serrations 7 of the adapter 5. The upper end of the adapter is in the form of a shank 9 onto which the prosthesis tube 4 is fitted, the bottom end of which rests upon an annular abutment surface 10 of the adapter 5. The bolt 6 passes through a slot 11 running lengthwise of the foot and having a width b corresponding to the bolt diameter d, and its head, forming its bottom end, thrusts a washer 12 against the bottom 1 a of the internal foot spring 1 which, in the area around the slot 11, is likewise in the form of a cylinder segment whose shape is adapted to the shape of the confronting face of the washer 12.

The prosthesis tube 4 together with the shank 9 of adapter 5 forms an annular gap which receives, in succession from the adapter abutment surface 10 upward, an end ring 13, an elastomer ring 14, a plastic intermediate ring 15, another elastomer ring 16, and a plastic upper end ring 17. Against the latter a driver 18, which is guided by the adapter shank 9 and held within the inner wall of the prosthesis tube, thrusts downwardly. The upper end of bolt 6 passes through the driver 18 and cup springs 19 mounted thereon, and is provided with a nut 20 which forms for the cup springs 19 the second abutment confronting the driver 18. Between the driver 18 and the nut 20 there is provided a device preventing rotation. Also, between the driver 18 and the prosthesis tube 4 a device preventing rotation is provided in the form of an elastomer ring 21 inserted between them.

After the (partial) loosening of the bolt 6, it is possible to set different heel levels by tilting the adapter 5 with respect to the spring 1 within the perpendicular plane defined by the slot 11. In the desired angular position the bolt 6 is then retightened so that the desired angular position is positively secured by the interlocking serrations 7 and 8. The rotation of the bolt 6, and hence of the adapter 5, is performed about an imaginary horizontal axis which in the embodiment is approximately in the area of the nut 20 and is perpendicular to the plane of drawing.

The bolt 6 binds all parts of the foot prosthesis together and secures their position with respect to their displacement in the direction of the longitudinal axis of the leg. But at the same time the bolt 6 also serves for applying the force clamping the prosthesis tube 4 to the adapter shank 9, since any tightening of the bolt 6 applies a downwardly directed force in the longitudinal direction of the bolt 6, thereby applying an axial force to the stack of rings disposed in the annular gap between prosthesis tube 4 and adapter shank 9. This application of force results in a deformation of the elastomer rings 14 and 16 which ultimately produce the said frictional clamping action. Thus the prosthesis tube 4 is secured with respect to the adapter shank 9 as regards longitudinal and torsional forces. At the same time, however, the result is a quick and easily releasable connection between the foot prosthesis and the prosthesis tube 4. The spring means formed by the cup springs 19 controls—without the use of a wrench—the torque that needs to be applied in order to tighten the screw.

As for its construction, the foot prosthesis can be used on the left side or on the right side.

The internal foot spring 1 serves to store energy during the rolling and the resultant flexure at its end tapering from the adapter 5. Any lateral slippage of the adapter 5 is prevented by the shape of the slot 11.

The insert wedge 2 serves to adapt the foot portion to the level of the heel; the tread damping can be varied by appropriate selection of the insert wedge. The cosmetic covering 3 permits easy adaptation to the foot size.

The prosthesis tube 4 serves to transfer forces along the axis of the leg to the foot prosthesis; by shortening the prosthesis tube 4 individual setting for the length of the leg is easily possible.

What is claimed is:

1. A jointless foot prosthesis comprising:
   (a) an internal foot spring extending from a heel to a forefoot of the foot prosthesis, the internal foot spring being enclosed in a cosmetic covering, the internal foot spring including a mating surface configured as an arcuate segment provided with serrations;
   (b) an adapter for releasably engaging a prosthesis tube, the adapter comprising:
      (1) a first portion configured as an arcuate segment provided with serrations to releasably engage the mating serrations of the foot spring;
      (2) a second portion configured as a shank for insertion into the prosthesis tube;
      (3) at least one elastomer ring disposed in an annular gap between the shank an the prosthesis tube when the shank is engaged with the tube; and
      (4) clamp means;
   (c) wherein a bolt passes through a slot extending along a portion of the length of the foot spring, the slot having a width sized to receive the bolt such that a first end of the bolt engages an underside of the foot spring and a second end of the bolt extends above the shank of the adapter and engages the clamp means; wherein by tightening the bolt, the bolt applies a vertical force on the clamp means which applies a vertical force on said at least one elastomer ring such that said at least one elastomer ring expands in a horizontal plane, thereby effecting an engagement between the prosthesis tube and the adapter.

2. The foot prosthesis according to claim 1, including a first ring and a second ring, wherein the at least one elastomer ring is disposed between the first and second ring.

3. The foot prosthesis according to claim 1, characterized in that the foot spring is supported on a replaceable insert wedge.

4. The foot prosthesis according to claim 3, characterized in that the insert wedge is held in a form-fitting manner between a bottom of the cosmetic covering and the foot spring.

5. The foot prosthesis according to claim 1, wherein said clamp means comprises a spring means and a thrust piece on said second portion of the adapter and apply a vertical force on said at least one elastomeric ring.

* * * * *